United States Patent [19]

Shin et al.

[11] Patent Number: 4,886,543
[45] Date of Patent: Dec. 12, 1989

[54] CRYOPROTECTANT COMPOSITION

[75] Inventors: Charles C. Shin; Nicolai A. Favstritsky; Ahmad Dadgar, all of West Lafayette, Ind.

[73] Assignee: Great Lakes Chemical Corporation, West Lafayette, Ind.

[21] Appl. No.: 216,126

[22] Filed: Jul. 7, 1988

[51] Int. Cl.$^4$ ............................................. A01N 43/08
[52] U.S. Cl. .......................................................... 71/88
[58] Field of Search ............................................ 71/88

[56] References Cited

U.S. PATENT DOCUMENTS 4,219,965 9/1980 Freebairn et al. ...................... 47/2
4,618,442 10/1986 Geary et al. ........................... 250/70

FOREIGN PATENT DOCUMENTS

2119653 A 5/1982 United Kingdom .

OTHER PUBLICATIONS

QO Chemicals, Inc., Bulletin 206-B-I, QO Tetrahydrofururyl Alcohol/THFA General Info. Properties Appl. Handling pp. 7-8.
QO Chemicals, Inc., Bulletin 206-B-II, QO Tetrahydrofurfuryl Alcohol/THFA An Environmentally Acceptable, Biodegradable, Water Miscible Solvent.
Allegretto, Using Polymers for Agricultural Frost Protection, Chemtech, vol. 14, pp. 152-155 (1984).
The Merck Index (1983) 9038.
Anon. Chem. Abst. vol. 81 (1974) 48636m.

*Primary Examiner*—Catherine L. Mills
*Attorney, Agent, or Firm*—Senniger, Powers, Leavitt and Roedel

[57] ABSTRACT

Aqueous plant cryoprotectant composition containing between about 0.005 and 25 wt. % tetrahydrofurfuryl alcohol, tetrahydrofurfuryl amine or mixtures thereof and method of increasing the resistance of plant tissue to damage caused by freezing conditions comprising applying to the plant tissue surfaces at ambient non-freezing temperatures an aqueous solution containing an effective amount of tetrahydrofurfuryl alcohol, tetrahydrofurfuryl amine or mixtures thereof.

12 Claims, No Drawings

CRYOPROTECTANT COMPOSITION

BACKGROUND OF THE INVENTION

This invention relates to plant cryoprotectant compositions and methods for preventing damage to plants caused by exposure to freezing temperatures for limited periods.

Freezing temperatures are a major cause of damage to plants and plant tissue. According to one estimate, approximately $1.5 billion of agricultural products are annually lost to freezing temperatures in the United States. In Florida alone, more than $3 billion of frost-damage to citrus trees has been reported over the last five years.

Numerous methods have been attempted to prevent damage to plants and plant tissue caused by freezing temperatures. One such method involves the development of hardy plant species, a laborious, time consuming and costly proposition. Other methods involve the use of fogs, smoke, protective foams, bags and the like to prevent the escape of heat from the plant. Still other methods involve the use of wind machines, heaters and/or irrigation. However, none of these approaches has proven to be both effective and commercially practical.

A different approach that has been attempted to prevent frost damage to plants involves treatment of the plant with a cryoprotectant composition. During the last 75 years, many compounds have been identified which exert cyroprotection when added to plant tissues. However, in order to be practically useful, such a composition must be non-toxic to plants, environmentally acceptable and relatively inexpensive. The center of research interest in this field has changed from early emphasis on small molecules that penetrate the cell, to more recent exploration of protective effects derived from very large non-penetrating compounds as they affect the properties of the external solution. However, none of these compounds are currently in wide-spread use. A few successful trial cases have been reported, but the chemicals employed have not been generally accepted.

SUMMARY OF THE INVENTION

Among the objects of the invention, therefore, may be noted the provision of a plant cryoprotectant composition that increases the hardiness of plants and plant tissue. Another object of this invention is the provision of a plant cryoprotectant composition which is relatively inexpensive, non-toxic, and environmentally acceptable. A further object of this invention is the provision of a method for the cryoprotection of plants and plant tissue.

Briefly, therefore, the present invention is directed to an aqueous plant and plant tissue cryoprotectant solution containing between about 0.005 and about 25 wt.% of a cryoprotectant component selected from the group consisting of tetrahydrofurfuryl alcohol, tetrahydrofurfuryl amine and mixtures thereof.

The invention is further directed to a method of increasing the resistance of plant tissue to damage caused by freezing conditions comprising applying to the plant tissue surfaces at an ambient non-freezing temperature, an aqueous solution containing an effective amount of a cryoprotectant component selected from the group consisting of tetrahydrofurfuryl alcohol, tetrahydrofurfuryl amine and mixtures thereof at least about 4 hours prior to the onset of such freezing conditions.

Other objects and features of this invention will be in part apparent and in part pointed out hereinafter.

DESCRIPTION OF THE PREFERRED EMBODIMENTS

In accordance with this invention, a plant cryoprotectant composition has been discovered which comprises an aqueous solution containing a cryoprotectant component selected from the group consisting of tetrahydrofurfuryl alcohol, tetrahydrofurfuryl amine or mixtures thereof. Preferably, the composition comprises between about 0.005 and about 25 wt% of the cryoprotectant component and most preferably comprises between about 0.1 and about 5 wt% of the cryoprotectant component.

Tetrahydrofurfuryl alcohol is a colorless, high boiling, primary alcohol having the following structure:

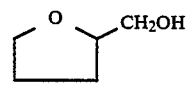

Tetrahydrofurfuryl amine is a colorless, high boiling primary amine having the following structure:

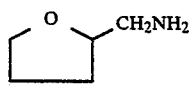

Although both tetrahydrofurfuryl alcohol and tetrahydrofurfuryl amine exhibit plant cryoprotectant properties, tetrahydrofurfuryl alcohol is preferred in accordance with the present invention. Tetrahydrofurfuryl alcohol is produced by hydrogenation of furfuryl alcohol and is marketed under the name THFA. As expected on the basis of its structure, tetrahydrofurfuryl alcohol exhibits behavior characteristics of both alcohols and ethers. Due to its cyclic ether structure, tetrahydrofurfuryl alcohol possesses distinctly unique solvent properties which are desirable for cryoprotecting agents, such as:

1. low volatility (vapor pressure 2.3 mm Hg at 39° C.),
2. non-damaging and non-toxic,
3. biodegradable,
4. easily absorbable,
5. ability to penetrate membranes,
6. considerable solubility in water in addition, to its ability to form multiple hydrogen bonds,
7. ability to dissolve electrolytes.

The resistance of plants and plant tissue to frost and low temperatures, including subfreezing temperatures, are increased for limited periods through the application of the cryoprotectant composition of this invention by spraying or dipping. For spraying, any suitable plant spray apparatus suitable for spraying aqueous solutions may be employed. The plants to be treated are thoroughly sprayed so that all of the plant tissue surfaces are completely covered. Due to the size or shape of a plant, a single application may require two or more sprayings.

The cryoprotectant composition is applied at ambient, non-freezing temperatures, i.e., the temperature of the air surrounding the plant or plant tissue is above 32° F. Preferably, the cryoprotectant composition is applied when the ambient air temperature is at least 35° F.

The cryoprotectant composition may be formulated and supplied to the user in concentrated form and diluted to the desired strength prior to application to the plant. No special handling or mixing steps are required. THFA and tetrahydrofurfuryl amine are stable in aqueous solution. Moreover, these compositions are stable to light and do not need to be stored in an opaque container nor prepared immediately prior to application.

Since an aqueous THFA or tetrahydrofurfuryl amine solution may not completely wet the surfaces of leaves of plants having waxy leaves, for some applications it is preferred that the cryoprotectant composition include a non-ionic surfactant. Two different surfactants, polyoxyethylene sorbitan monolaurate (Tween 20) and polyoxyethylene sorbitan monooleate (Tween 80) have been found to improve the wetability of the composition and thereby improve its effectiveness. When non-ionic surfactants are used, it is preferred that the cryoprotectant composition contain between about 0.05 and about 0.5 wt.% non-ionic surfactant.

The effectiveness of the cryoprotectant composition is not diminished by the inclusion of such compounds as organic/inorganic fertilizers, pesticides, plant hormones, growth regulators, other polymers, and coating materials. For instance, it has been found that the composition is compatible with urea; the introduction of urea via a 1:1 THFA:UREA mixture, did not affect the wetability or the effectiveness of the agent. Nevertheless, it is presently preferred that the cryoprotectant composition have an essential absence of pesticides.

Although the cryoprotectant composition of this invention may be applied to the plants immediately prior to exposure to freezing conditions, it is preferred that the composition be applied between about 4 hours and 1 week prior thereto. Moreover, for optimal results it is preferred that the cryoprotectant composition be applied twice prior to the onset of freezing temperatures, the first application being made between about several days and about one week prior to the onset of freezing temperatures and constituting a conditioning application. The second application is then preferably made a sufficient period prior to the onset of freezing temperatures to permit absorption of the composition, e.g., at least about 4 hours.

For maximum protection during the spring frost season, it may be desirable to apply the cryoprotectant composition weekly to minimize any damage that might be caused by a sudden occurrence of freezing temperatures. Nevertheless, due to this agent's high penetrability into some plant tissues, it may be possible to apply this invention immediately before the exposure to freezing temperatures if the plant can tolerate a high concentration of the agent.

The following examples illustrate the invention. All percentages are by weight unless otherwise indicated.

EXAMPLE 1

A. Materials and Methods

Plants were sprayed with the indicated antifrost agents and set out at room temperature for a period of time for conditioning. Several hours prior to exposure to freezing temperatures, a second application of the antifrost agent was given to some of the plants. The period between the first application and the second application is referred to hereinafter as the conditioning time and the period between the second application and the placement in the freezer, as described below, is referred to as the absorption time. For those instances in which there was only a single application and the elapsed time between the application and placement in the freezer exceeded 12 hours, that period is referred to as conditioning time. If the period was less than 12 hours, it is referred to as absorption time.

The pots holding the conditioned plants were fitted into a polyurethane insulated box having circular openings in the top. Each opening was sized to snugly receive a single pot holding a conditioned plant and the box had sufficient depth so that substantially the entire pot was contained within the insulated box while the conditioned plant stood outside the box. The box was heated by circulation of room temperature air through its interior. The insulated box holding the plants was placed inside a commercial freezer that was modified to achieve dynamic temperature control to within 0.01° C. The air temperature inside the freezer was monitored on a CRT screen and also recorded on a chart recorder. The air temperature inside the freezer was gradually reduced (4° C./hr) from an initial temperature (10° C.) until the set point temperature was achieved. The set temperature was maintained for a period of three or four hours and then gradually warmed (4° C./hr) to a final temperature ($\geq 5°$ C.). During the period that the plant was inside the freezer, the insulated box protected the roots from freezing somewhat the same, but less efficiently, as the ground does in nature.

After removal from the freezer, the plants were inspected and a binary result recorded, i.e., either the plants survived or were permanently damaged. Visual observance could easily differentiate the effectiveness of the various antifrost agents tested. For each test, if all of the plants survived the initial cold, the plants were removed from the freezer, the pots were allowed to return to room temperature and the plants were then returned to the freezer where the air temperature was then set at a lower temperature than the previous run. This process was repeated until a temperature was reached at which some of the plants did not survive. The useable temperature range and relative effectiveness of the antifrost agents was thus determined.

The maximum time for exposure to freezing temperatures was limited to 6 hours because beyond that, the pots could not be kept from freezing. Instead, the tests in which plants survived exposure for 6 hours were repeated a few times to determine whether the plants could survive longer exposure, like those encountered under actual conditions in the field.

The antifrost agents evaluated were the following:
1. tetrahydrofurfuryl alcohol dissolved in deionized (DI) water to make 0.5% and 5% THFA aqueous solutions;
2. 0.1 parts of a surfactant, polyoxyethylene sorbitan monolaurate (Tween 20) and 0.5 parts tetrahydrofurfuryl alcohol dissolved in 99.4 parts DI water to make an aqueous 0.5% THFA+0.1% Tween 20 solution.
3. 0.5 parts urea and 0.5 parts tetrahydrofurfuryl alcohol dissolved in 99 parts DI water to make an aqueous 0.5% THFA+0.5% urea solution.
4. polyethyleneglycol polysiloxane copolymer having a PG/PS monomer ratio of 5.3/1 prepared according to the method set forth in D. J. Bannister, et al "Water Soluble Siloxane: Poly (Erthylene Glycol) Comb Polymer", *Journal of Polymer Science: Polymer Letters Ed.*, Vol. 23, p. 465–467 (1985), dissolved in DI water to make aqueous 0.5% and 5% PS/PEG solutions;

5. A non-ionic surfactant GOLDEN FROST FREE (Plant Products Corporation; Vero Beach Fla.), dissolved in DI water to make aqueous 0.3% and 0.29% Golden Frost Free solutions;
6. a polyoxyethylenated polyoxypropylene copolymer (molecular weight 4500) obtained from Diamond Shamrock Corporation under the trademark Monolan 4500, dissolved in DI water to make aqueous 0.3% and 0.4% solutions designated PPC707;
7. equal parts tetrahydrofurfuryl alcohol and polyethyleneglycol polysiloxane copolymer (subpart 4, above) dissolved in DI water to make an aqueous 0.25% THFA+0.25% PS/PEG solution ("0.5% mixture");
8. tetrahydrofurfuryl amine dissolved in DI water to make an 0.5% tetrahydrofurfuryl aqueous solution.
9. furfuryl alcohol dissolved in DI water to make an 0.5% furfuryl alcohol aqueous solution.
10. 1,2-propanediol dissolved in DI water to make an 0.5% 1,2-propanediol aqueous solution.

B. Evaluation of the Antifrost Agents with Impatiens

Garden plants of the impatiens variety were sprayed with various antifrost agents listed in part A (as indicated in Table I). Each plant was treated twice with the respective antifrost agent and was allowed five days between the two applications for conditioning. After the second spray, a six hour absorption period was provided. The plants were then placed in the freezer and the temperature was lowered to the set point temperature (−3.5° C.), maintained there for three hours, and then raised to 8° C. over a three hour period.

As shown in table I, the impatiens treated with 0.5% THFA and 0.5% PS/PEG survived whereas the plants treated with PPC707 and those exposed without any antifrost treatment died.

TABLE I

| FREEZING DAMAGE TEST RESULTS FOR IMPATIENS EXPOSED TO −3.5° C. FOR THREE HOURS | | |
|---|---|---|
| Antifrost Agent | Conditioning/Absorption Time | Results |
| Blank | —/— | Died |
| 0.5% PS/PEG | 5 days/6 hours | Survived |
| 0.5% THFA | 5 days/6 hours | Survived |
| 0.3% Golden Frost Free | 5 days/6 hours | Died |
| 0.3% PC707 | 5 days/6 hours | Died |

C. Second Evaluation of the Antifrost Agents with Impatiens

The procedure provided in part B was repeated, except that some of the plants were given a single application of the compositions having a higher concentration of the antifrost agents to determine whether these agents are effective with only one treatment. The remainder of the plants were given two applications as indicated in Table II. The results listed in Table II indicate that impatiens treated once with either 5% PS/PEG or 5% THFA survived the freezing temperatures. Again, plants treated with 0.5% PS/PEG or 0.5% THFA survived, while those treated with PPC707 or Golden Frost Free, like the ones left without any antifrost protection, did not survive.

TABLE II

| FROST DAMAGE TEST FOR IMPATIENS EXPOSED TO −3.5° C. FOR THREE HOURS | | |
|---|---|---|
| Antifrost Agent | Conditioning/Absorption Time | Results |
| Blank | —/— | Died |
| 0.5% PS/PEG | —/6 hours | Died |
| 5% PS/PEG | —/6 hours | Survived |
| 5% PS/PEG | 2 days/— | Survived |
| 0.5% Mixture | 5 days/6 hours | Survived |
| 0.5% THFA | 7 days/6 hours | Survived |
| 5% THFA | —/6 hours | Survived |
| 0.4% PPC707 | 7 days/6 hours | Died |
| 0.29% Golden Frost Free | 7 days/6 hours | Died |

D. Evaluation of the Antifrost Agents with Fuchsias

The procedure is part B was repeated except that the garden plants employed for this test were fuchsias. The fuchsias were treated with various antifrost agents (as indicated in Table III) and then exposed to a freezing temperature of −4° C. for three hours. The test results in Table III show that Golden Frost Free, 0.5% THFA, 0.5% PS/PEG, and 5% THFA are effective in protecting fuchsias from the ravages of frost.

TABLE III

| FROST DAMAGE TESTS FOR FUCHSIAS EXPOSED TO −4° C. FOR THREE HOURS | | |
|---|---|---|
| Antifrost Agent | Conditioning/Absorption Time | Results |
| Blank | —/— | Died |
| Golden Frost Free | 5 days/4 hours | Survived |
| 0.5% THFA | 5 days/4 hours | Survived |
| 0.5% PS/PEG | 5 days/4 hours | Survived |
| 5% THFA | —/4 hours | Survived |
| 5% PS/PEG | —/4 hours | Died |

E. Second Evaluation of the Antifrost Agents with Fuchsias

Freezing survival tests for fuchsias were repeated in the same manner as above, except that the freezing temperature in this experiment was maintained at −5° C. for four hours. The results listed in Table IV indicate that PPC707, Golden Frost Free, and PS/PEG are not individually as effective as is THFA for fuchsias. Fuchsias treated with 5% THFA for 4 hours prior to their exposure to −5° C. survived, as did those treated twice with 0.5% THFA. Fuchsias sprayed with 5% THFA for only 2 hours prior to exposure for freezing conditions also survived.

TABLE IV

| FREEZING SURVIVAL TESTS OF FUCHSIAS TESTED AT −5° C. FOR FOUR HOURS | | |
|---|---|---|
| Antifrosting Agent | Conditioning/Absorption Time | Results |
| 0.4% PPC707 | 7 days/4 hours | Died |
| 0.4% Golden Frost Free | 7 days/4 hours | Died |
| 0.5% PS/PEG | 7 days/4 hours | Died |
| 0.5% Mixture | 7 days/4 hours | Died |
| 0.5% THFA | 7 days/4 hours | Died |
| 5% THFA | —/4 hours | Survived |
| 5% THFA | —/2 hours | Survived |
| 5% THFA | 1 day/— | Survived |
| 5% THFA | 8 days/— | Survived |

F. Third Evaluation of the Antifrost Agents with Fuchsias

Here, the freezing temperature was lowered to −6° C. and maintained there for 4 hours. The fuchsias tested in this example were those which survived the previous freezing tests. The purpose of this test was to determine whether the plants could survive longer exposures, like those encountered under actual conditions in the field.

TABLE V

FREEZING SURVIVAL TESTS FOR FUCHSIAS EXPOSED TO −6° C.

| Antifrost Agent | Total Exposure Time | Results |
|---|---|---|
| 0.5% THFA | 8 hours | Survived |
| 0.5% THFA | 12 hours | Survived |
| 5% THFA | 8 hours | Survived |
| 5% THFA | 12 hours | Survived |

G. Evaluation of the Antifrost Agents with Coleuses

The garden plant coleus is very delicate and sensitive to freezing temperatures due to the high water content of its tissues. A set of six coleuses treated with different antifrost agents was exposed to −7° C. for four hours. The results of this test are listed in Table VI. The plants treated twice with 0.5% THFA survived. Coleuses treated with 5% THFA showed signs of antifrost agent rejection and were not included in this frost survival test.

TABLE VI

FREEZING SURVIVAL TEST FOR COLEUSES EXPOSED TO −7° C. FOR FOUR HOURS

| Antifrost Agent | Conditioning/Absorption Time | Results |
|---|---|---|
| Blank | —/— | Died |
| 0.29% Golden Frost Free | 3 days/2 hours | Died |
| 0.3% PPC707 | 3 days/2 hours | Died |
| 0.5% Mixture | 3 days/2 hours | Died |
| 0.5% THFA | 3 days/2 hours | Survived |
| 0.5% THFA | 3 days/2 hours | Survived |

H. Evaluation of Cryoprotectant Composition containing a Surfactant or Urea.

The poor wetability of aqueous THFA solutions on some of the waxy-leaved plants such as peppers or tomatoes delays absorption of this solution into the plant tissues. In order to improve the wetability, two different surfactants selected from the EPA inert compound list were tested. Both surfactants dramatically improved the cryoprotectant composition's wetability. Both surfactants contained potential known cryoprotectant ingredients such as sorbitol and polyoxyethylene. Since Tween 20 (polyoxyethylene sorbitan monolaurate) was found to mix with the cryoprotectant composition much more easily than Tween 80 (polyoxyethylene sorbitan monooleate), tween 20 was used in the frost damage tests. Six tomatoes treated with aqueous 0.5% THFA solutions containing different additives were exposed to −5° C. for 4 hours. The results of this test are listed in Table VII. The incorporation of a mere 0.1% surfactant not only dramatically improved the wetability but also reduced the absorption time of the agent. The addition of urea did not seem to improve the effectiveness of the agent, but the test results do indicate that this agent is compatible with the fertilizer.

TABLE VII

FREEZING SURVIVAL TEST RESULTS FOR TOMATOES EXPOSED TO −5° C. FOR FOUR HOURS

| Antifrost Agent | Additve | Results |
|---|---|---|
| 0.5% THFA | None | Survived |
| 0.5% THFA | 0.1% Tween 20 | Survived |
| 0.5% THFA | 0.5% urea | Survived |
| 0.5% THFA | 0.5% urea + 0.1% Tween 20 | Survived |
| Blank | Blank | Died |

I. Evaluation of the Antifrost Agent with Peppers

In this experiment, peppers were treated with different antifrost agents and were exposed to −6° C. for 4 hours. The test results listed in Table VIII show that the plants treated with Golden Frost Free, 0.5% THFA with 0.1% Tween 20, and 0.5% THFA mixed in with 0.1% Tween 20 and 0.5% urea, survived. One interesting observation here is that 0.5% THFA did not prevent freezing damage to these plants. The reason may be the poor wetability of THFA alone on this plant. However, the effectiveness of THFA only on pepper plants was confirmed through additional tests.

TABLE VIII

FREEZING SURVIVAL TEST RESULTS FOR PEPPER TREATED WITH VARIOUS ANTIFROST AGENTS AFTER EXPOSURE TO −6° C. FOR 4 HOURS

| Antifrost Agent | Conditioning/Absorption Time | Results |
|---|---|---|
| 0.5% THFA | 3 days/3 hours | Died |
| 0.5% THFA + 0.1% Tween 20 | 3 days/3 hours | Survived |
| 0.5% THFA + 0.5% urea + 0.1% Tween 20 | 3 days/3 hours | Survived |
| 0.29% Golden Frost Free | 3 days/3 hours | Survived |

J. Further Evaluation of the Cryoprotectant Compositions with Impatiens

Freezing survival tests for impatiens were continued using aqueous solutions of other furfuryl group compounds to evaluate their effectiveness as antifrost agents. The impatiens used in this evaluation and in the evaluation of subpart K, infra were grown in a much warmer environment than the evaluations reports in subparts A-I, supra. None of the impatiens treated with antifrost agents and conditioned at room temperature for 3 to 10 days survived freezing temperatures of −3.5° C. to −6.0° C., indicating that these plants should have been acclimatized at near freezing temperatures before they were exposed to freezing conditions.

Two impatiens were sprayed with 0.5% THFA, two with 0.5% tetrahydrofurfuryl amine, and one with 0.5% furfuryl alcohol. A control blank was not treated. After standing for 7 days for conditioning, these plants were acclimated to 1° C. for 24 hours. Then the plants were sprayed once more with the respective antifrost compositions and sufficient time was allowed for the agents to be absorbed completely. Finally the plants were exposed to a temperature of −3.5° C. for 4 hours. As shown in Table IX, the plants treated with THFA or tetrahydrofurfuryl amine survived whereas the others died.

TABLE IX

FREEZING SURVIVAL TESTS FOR IMPATIENS TREATED WITH AQUEOUS SOLUTION OF FURFURYL GROUP COMPOUND AFTER EXPOSURE TO −3.5° C. FOR 4 HOURS

| Antifrost Agent | Conditioning/Acclimating/Absorption Time | Result |
|---|---|---|
| Blank | —/24 hours/— | Died |
| 0.5% THFA | 7 days/24 hours/4 hours | Survived |
| 0.5% THFA | 7 days/24 hours/4 hours | Survived |
| 0.5% Tetrahydrofurfuryl Amine | 7 days/24 hours/4 hours | Survived |
| 0.5% Tetrahydrofurfuryl Amine | 7 days/24 hours/4 hours | Survived |
| 0.5% Furfuryl Alcohol | 7 days/24 hours/4 hours | Died |

K. Further Evaluation of the Cryoprotectant Compositions with Impatiens

The procedure outlined in subpart J was repeated except that another potential candidate, 1,2-propanediol was compared with THFA and tetrahydrofurfuryl amine. 1,2-propanediol, a poly-alcohol, is the best reported to date for its glass forming tendency and stability in the amorphous state, which are the properties required for good cryoprotecting agents. The frost damage test results in Table X show that tetrahydrofurfuryl alcohol and amine are better antifrost agents than 1,2-propanediol.

TABLE X

FREEZING SURVIVAL TEST RESULTS FOR IMPATIENS AFTER EXPOSURE TO −4° C. FOR 4 HOURS

| Antifrost Agent | Conditioning/Acclimating/ Absorption Time | Result |
|---|---|---|
| Blank | —/24 hours/— | Died |
| 0.5% 1,2-propanediol | 7 days/24 hours/4 hours | Died |
| 0.5% 1,2-propanediol | 7 days/24 hours/4 hours | Died |
| 0.5% Tetrahydro-furfuryl Amine | 7 days/24 hours/4 hours | Survived |
| 0.5% THFA | 7 days/24 hours/4 hours | Survived |
| 0.5% THFA | 7 days/24 hours/4 hours | Survived |

In view of the above, it will be seen that the several objects of the invention are achieved.

As various changes could be made in the above compositions and methods without departing from the scope of the invention, it is intended that all matter contained in the above description shall be interpreted as illustrative and not in a limiting sense.

What is claimed:

1. A method of increasing the resistance of plant tissue to damage caused by freezing conditions comprising applying to the plant tissue surfaces at ambient non-freezing air temperatures at least about four hours prior to exposure to such freezing conditions an aqueous solution containing an effective amount of tetrahydrofurfuryl alcohol, tetrahydrofurfuryl amine or mixtures thereof as a cryoprotectant component.

2. A method as set forth in claim 1 wherein the aqueous solution contains between about 0.005 and about 25 wt% tetrahydrofurfuryl alcohol.

3. A method as set forth in claim 1 wherein the aqueous solution contains between about 0.1 and about 5 wt% tetrahydrofurfuryl alcohol.

4. A method as set forth in claim 1 wherein said aqueous solution contains a non-ionic surfactant.

5. A method as set forth in claim 4 wherein said aqueous solution contains between about 0.05 and about 0.5 wt.% non-ionic surfactant.

6. A method as set forth in claim 5 wherein said non-ionic surfactant is polyoxyethylene sorbitan monolaurate or polyethylene sorbitan monooleate.

7. A method as set forth in claim 1 wherein the aqueous solution contains between about 0.005 and about 25 wt.% tetrahydrofurfuryl amine.

8. A method as set forth in claim 1 wherein the aqueous solution contains between about 0.1 and about 5 wt.% tetrahydrofurfuryl amine.

9. A method for preventing damage to plants caused by exposure to freezing conditions comprising applying to the plant surfaces at ambient non-freezing temperatures at least about four hours prior to exposure to such freezing conditions an aqueous cryoprotectant solution containing an effective amount of tetrahydrofurfuryl alcohol.

10. A method as set forth in claim 9 wherein the aqueous solution contains between about 0.1 and about 5 wt.% tetrahydrofurfuryl alcohol.

11. A method as set forth in claim 9 wherein the aqueous solution contains between about 0.05 and about 0.5 wt.% non-ionic surfactant.

12. A method as set forth in claim 12 wherein the non-ionic surfactant is polyoxyethylene sorbitan monolaruate or polyethylen sorbitan monooleate.

* * * * *